United States Patent
Xu

(10) Patent No.: US 9,688,685 B2
(45) Date of Patent: Jun. 27, 2017

(54) METHOD FOR PREPARING VOLASERTIB AND INTERMEDIATE THEREOF

(71) Applicant: SUZHOU MIRACPHARMA TECHNOLOGY CO., LTD., Suzhou (CN)

(72) Inventor: Xuenong Xu, Suzhou (CN)

(73) Assignee: SUZHOU MIRACPHARMA TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 15/361,248

(22) Filed: Nov. 25, 2016

(65) Prior Publication Data

US 2017/0073350 A1 Mar. 16, 2017

Related U.S. Application Data

(63) Continuation of application No. PCT/CN2015/077897, filed on Apr. 30, 2015.

(30) Foreign Application Priority Data

May 26, 2014 (CN) .......................... 2014 1 0225833

(51) Int. Cl.
*C07D 475/04* (2006.01)
*C07D 487/04* (2006.01)
*C07D 475/00* (2006.01)
*C07D 295/135* (2006.01)

(52) U.S. Cl.
CPC ....... *C07D 487/04* (2013.01); *C07D 295/135* (2013.01); *C07D 475/00* (2013.01)

(58) Field of Classification Search
CPC .................................................... C07D 475/04
See application file for complete search history.

(56) References Cited

FOREIGN PATENT DOCUMENTS

| WO | 2004076454 A1 | 9/2004 |
| WO | 2006018220 A2 | 2/2006 |
| WO | 2007090844 A1 | 8/2007 |
| WO | 2009019205 A1 | 2/2009 |

*Primary Examiner* — Bruck Kifle
(74) *Attorney, Agent, or Firm* — Perkins Coie LLP

(57) ABSTRACT

Disclosed is a method for preparing Volasertib (I), comprising the following steps: an intermediate 2-amino-7-ethyl-7,8-dihydro-5-methyl-8-isopropyl-(7R)-6(5H)-pteridinone (II) is nucleophilically substituted with an intermediate N-[trans-4-[4-(cylopropylmethyl)-1-piperazinyl]cyclohexyl]-4-halo-3-methoxylbenzamide (III), so as to prepare Volasertib (I). The preparation method has a simple process, mild conditions and few side effects, which meets the requirements for industrial enlargement. In addition, also disclosed are an intermediate 2-amino-7-ethyl-7,8-dihydro-5-methyl-8-isopropyl-(7R)-6(5H)-pteridinone (II) and an intermediate N-[trans-4-[4-(cylopropylmethyl)-1-piperazinyl]cyclohexyl]-4-halo-3-methoxylbenza-mide (III) of Volasertib and the preparation methods thereof.

9 Claims, No Drawings

METHOD FOR PREPARING VOLASERTIB AND INTERMEDIATE THEREOF

CROSS REFERENCE TO RELATED APPLICATION

This application is a continuation of PCT/CN2015/077897 filed Apr. 30, 2015, which claims priority to CN 201410225833.8 filed May 26, 2014, both of which are incorporated herein by reference.

TECHNICAL FIELD

This invention relates to the technical field of organic synthesis route design and preparation of API and intermediates, in particular, to the method for preparing volasertib and intermediate thereof.

BACKGROUND ART

Volasertib is an experimental polo-like kinase (Plk) inhibitor researched and developed by Boehringer Ingelheim, which was awarded breakthrough therapy and orphan drug by FDA and FDA in September 2013 and April 2014, respectively. It is used for the treatment of patients with acute myeloid leukemia (AML) aged 65 years and older who are not eligible for intensive induction chemotherapy. Since this drug is not officially launched in China, it has no standard Chinese name. Volasertib is designed to inhibit the activity of regulatory cell mitogenase Plk1, which can prolong the time of cell cycle arrest and lead to apoptosis.

The chemical name of volasertib (Volasertib, I) is N-[trans-4-[4-(cyclopropylmethyl)-1-piperazinyl]cyclohexyl]-4-[[(7R)-7-ethyl-5,6,7,8-tetrahydro-5-methyl-8-isopropyl-6-oxo-2-pteridinyl]amino]-3-methoxybenzamide.

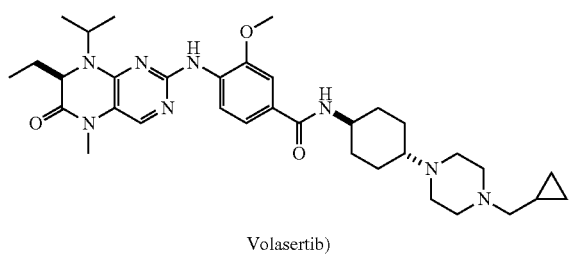

Volasertib)

The world patents WO2004/076454, WO2006/018220, WO2007/090844 and WO2009/019205 researched by Boehringer Ingelheim disclosed the preparation method of volasertib and its analogs. Although the preparation method of intermediate is different, the target product is produced by condensation reaction of the intermediate 2-chloro-7-ethyl-7,8-dihydro-5-methyl-8-isopropyl-(7R)-6(5H)-pteridinone (A) and N-[trans-4-[4-(cyclopropylmethyl)-1-piperazinyl]cyclohexyl]-4-amino-3-methoxybenzamide (B) under acidic conditions.

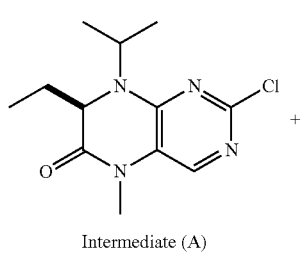

Intermediate (A)

+

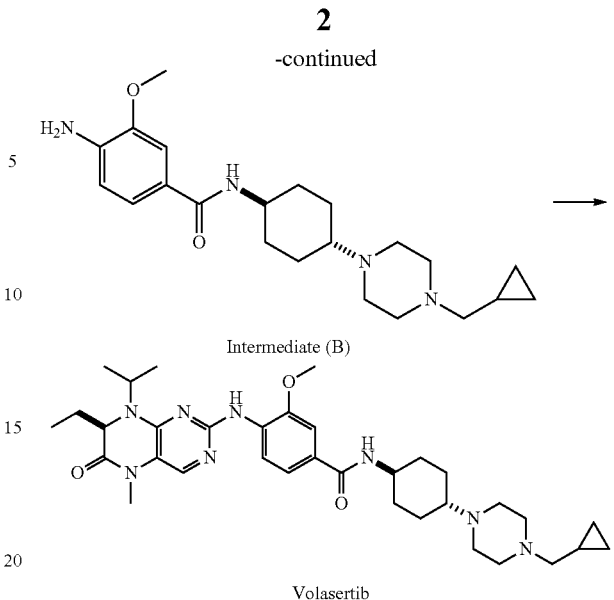

Intermediate (B)

Volasertib

The above literatures also disclosed the route for preparing intermediate (A):

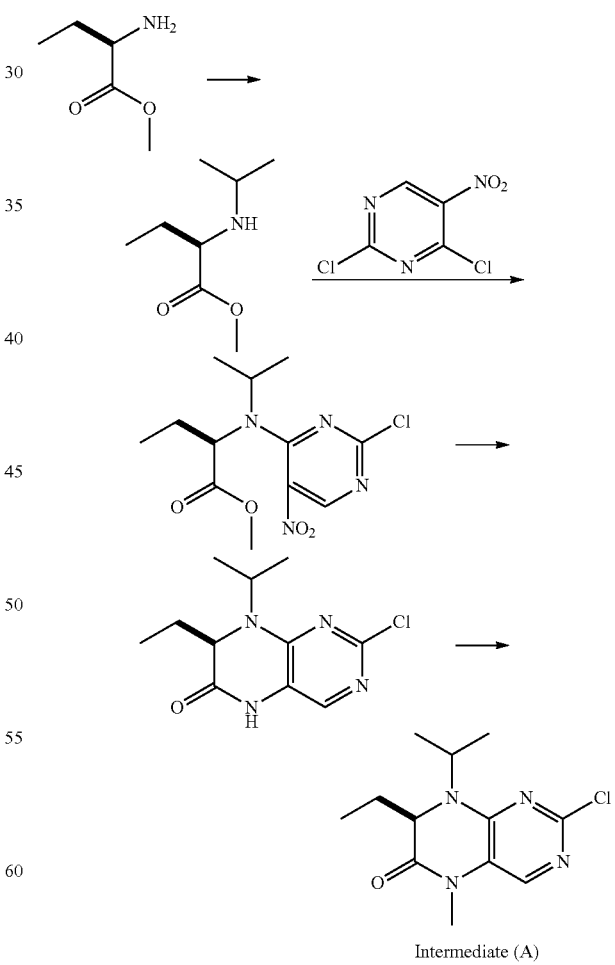

Intermediate (A)

The intermediate (B) is prepared in two ways: the first one, the intermediate (B) is obtained from the starting material 1,4-cyclohexylamine alcohol after amidation, oxidation, condensation reduction and nitro reduction.

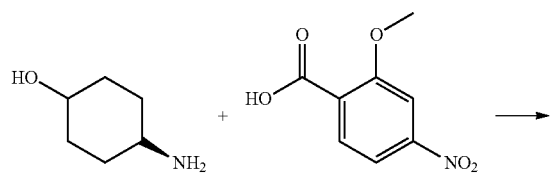

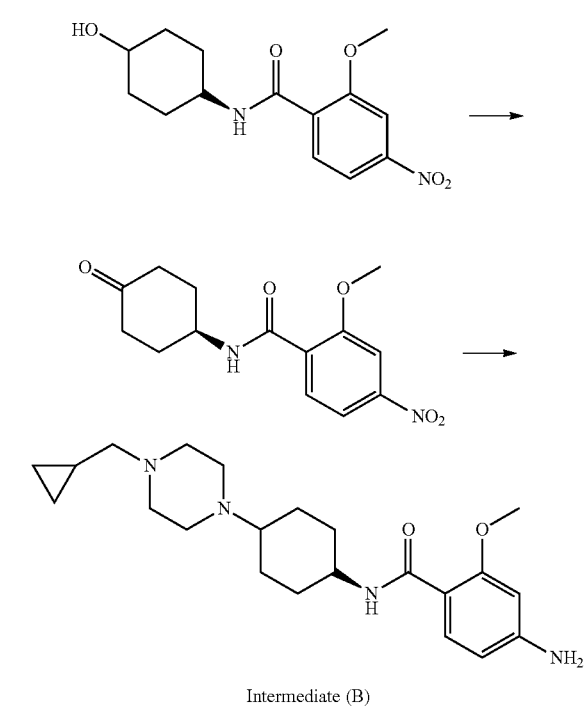

Intermediate (B)

The second one, the intermediate (B) is obtained from the starting material N-cyclohexylmethylpiperazine after condensation reduction, hydrolysis and salification, amidation and nitro reduction.

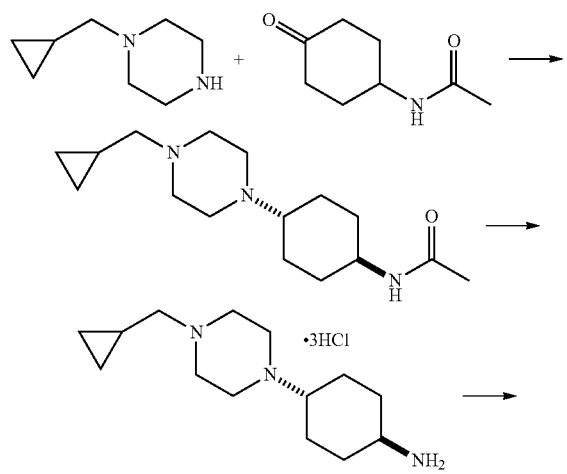

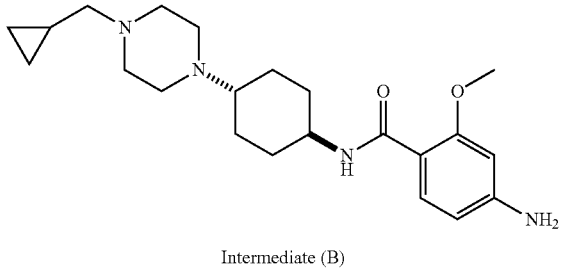

Intermediate (B)

By investigating the synthesis routes of intermediates (A), (B) and volasertib, the molecular structures of intermediates (A), (B) and volasertib contain many amino functional groups, when condensation, amidation and reduction reactions occur, the competitive side effects may happen in primary amine on cyclohexylamine, secondary amine on piperidine ring and primary amine on benzene ring, which will increase the difficulty of purification and reduce the total yield. Therefore, to seek a kind of synthesis route and preparation method of volasertib and intermediate thereof composed of classical unit reactions that can reduce side effects is of great practical significance for the industrialization of volasertib.

SUMMARY OF THE INVENTION

In order to overcome the drawbacks of the prior art, the object of the invention is to provide an improved method for the preparation of volasertib (I) according to the green chemistry synthesis concept. The preparation method has a simple process, mild conditions and few side effects, which meets the requirements for industrial enlargement. In addition, the invention further provides two intermediates that can be used for preparation of volasertib and preparation methods thereof.

In order to achieve the above object, the present invention provides the following main technical solutions: A method for preparing volasertib (Volasertib, N-[trans-4-[4-(cyclopropylmethyl)-1-piperazinyl]cyclohexyl]-4-[[(7R)-7-ethyl-5,6,7,8-tetrahydro-5-methyl-8-isopropyl-6-oxo-2-pteridinyl]amino]-3-methoxybenzamide, I),

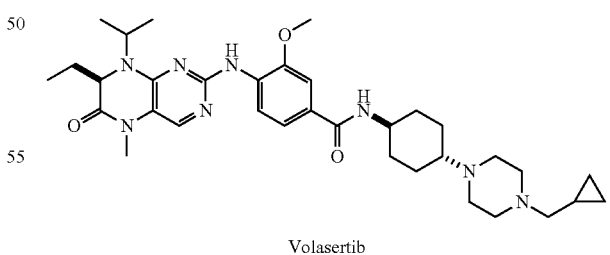

Volasertib wherein the preparation method comprises the following steps: an intermediate 2-amino-7-ethyl-7,8-dihydro-5-methyl-8-isopropyl-(7R)-6(5H)-pteridinone (II) is nucleophilically substituted with an intermediate N-[trans-4-[4-(cyclopropylmethyl)-1-piperazinyl]cyclohexyl]-4-halo-3-methoxylbenzamide (III), so as to prepare Volasertib (I).

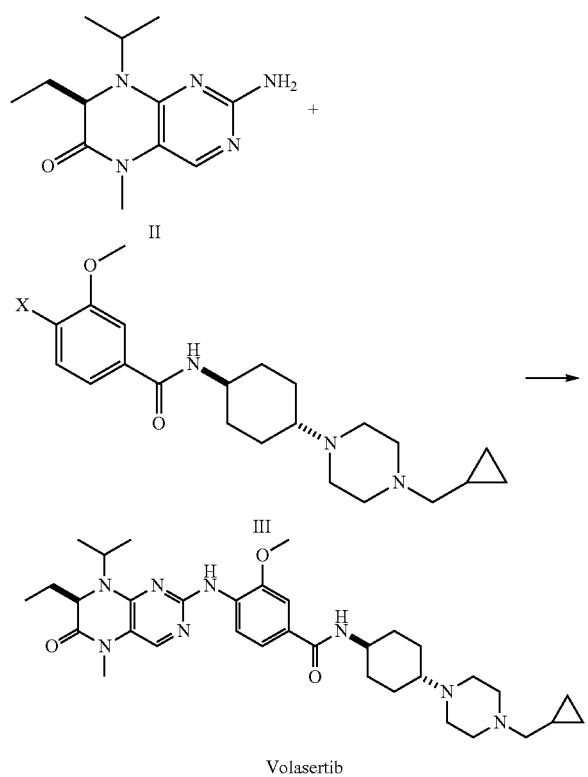

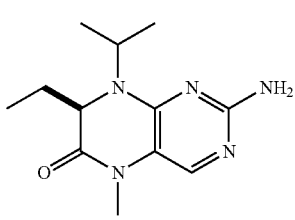

In addition, the invention further provides the following additional technical solutions:

The catalyst of the nucleophilic substitution reaction is cuprous iodide, zinc iodide, stannous chloride, palladium chloride, or silver iodide, preferably cuprous iodide.

The cocatalyst of the nucleophilic substitution reaction is 8-hydroxyquinoline, 2,6-dimethyl pyridine, 4-dimethylaminopyridine, N-methylmorpholine, N-ethylmorpholine, 1,5-diazabicyclo [4.3.0]-non-5-ene, 1,8-diazabicyclo [5.4.0]-undec-7-ene or 1,4-diazabicyclo [2.2.2] octane, preferably 8-hydroxyquinoline or 1,8-diazabicyclo [5.4.0]-undec-7-ene.

The solvent of the nucleophilic substitution reaction is xylene,dioxane,dimethylsulfoxide, N,N-dimethylformamide or N,N-dimethylacetamide, preferably dimethylsulfoxide or N,N-dimethylformamide.

The temperature of the nucleophilic substitution reaction is 100-160° C., preferably 110-150° C.

Further, the present invention provides a volasertib intermediate, wherein the chemical name is 2-amino-7-ethyl-7,8-dihydro-5-methyl-8-isopropyl-(7R)-6(5H)-pteridinone, and the chemical formula is as shown in formula (II):

The method for preparing the volasertib intermediate (II) comprising the following steps: 2-chloro-7-ethyl-7,8-dihydro-5-methyl-8-isopropyl-(7R)-6(5H)-pteridinone(IV) is subjected to an amination reaction to obtain 2-(N-allyl)amino-7-ethyl-7,8-dihydro-5-methyl-8-isopropyl-(7R)-6 (5H)-pteridinone(V), and the compound (V) is subjected to a reduction reaction to obtain the volasertib intermediate 2-amino-7-ethyl-7,8-dihydro-5-methyl-8-isopropyl-(7R)-6 (5H)-pteridinone (II).

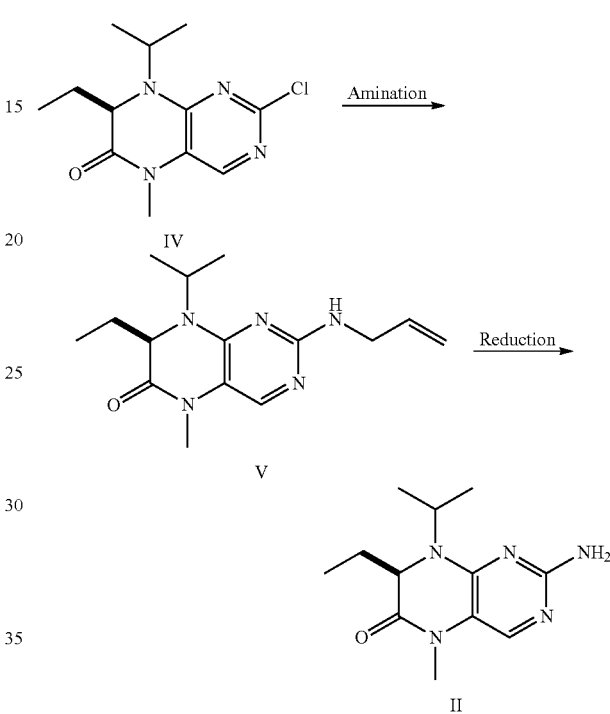

Further, the present invention provides another volasertib intermediate, wherein the chemical name is N-[trans-4-[4-(cylopropylmethyl)-1-piperazinyl]cyclohexyl]-4-halo-3-methoxylbenzamide, and the chemical formula is as shown in formula (III):

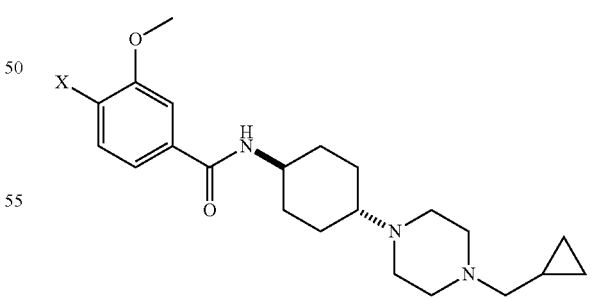

The method for preparing the volasertib intermediate (III) comprising the following steps: trans-4-[4-(cyclopropylmethyl)-1-piperazinyl]cyclohexylamine trihydrochloride(VI) and 3-methoxy-4-halo-benzoyl chloride(VII) have an amidation reaction to obtain the volasertib intermediate N-[trans-4-[4-(cylopropylmethyl)-1-piperazinyl]cyclohexyl]-4-halo-3-methoxylbenzamide (III).

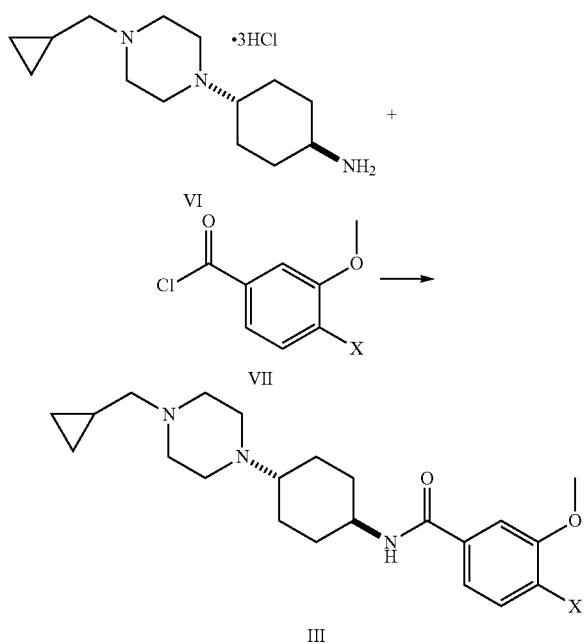

The halogen in the intermediate N-[trans-4-[4-(cylopropylmethyl)-1-piperazinyl]cyclohexyl]-4-halo-3-methoxyl-benzamide (III) is fluorine, chlorine, bromine or iodine, preferably bromine or iodine.

Compared to the prior art, the preparation method of volasertib and intermediates thereof in the invention has a simple process, mild conditions and few side effects, which meets the requirements for industrial enlargement.

DETAILED DESCRIPTIONS OF THE PREFERRED EMBODIMENTS

The invention is further described in details in combination with several preferred embodiments. The synthesis of raw materials of 2-chloro-7-ethyl-7,8-dihydro-5-methyl-8-isopropyl-(7R)-6(5H)-pteridinone(IV) and trans-4-[4-(cyclopropylmethyl)-1-piperazinyl]cyclohexylamine trihydrochloride(VI) can refer to the preparation methods of the same compounds in the world patent WO2007090844. The synthesis of 3-methoxy-4-halo-benzoyl chloride (VII) can refer to the preparation methods of the same and similar compounds described in the Archiv der Pharmazie (Issue 1, Volume 318, p 78-84) and Journal of Natural Products (Issue 10, Volume 76, p 1916-1922).

Embodiment I

Under nitrogen atmosphere, 2-amino-7-ethyl-7,8-dihydro-5-methyl-8-isopropyl-(7R)-6(5H)-pteridinone (II) (1.17 g, 5 mmol), N-[trans-4-[4-(cyclopropylmethyl)-1-piperazinyl]cyclohexyl]-4-bromo-3-methoxybenzamide (III) (2.25 g, 5 mmol), cuprous iodide (142 mg, 0.75 mmol), 8-hydroxyisoquinoline (220 mg, 0.75 mmol), potassium carbonate (760 mg, 5.5 mmol) and 50 mL N,N-dimethylformamide were added to a three-necked bottle, heated to 100° C., stirred to dissolve, then added with triethylamine (75 mg, 0.75 mmol), continued to heat to 140° C., reacted for 15 hours, to complete the reaction detected by TLC. The resulting solution was cooled down to 50-60° C. and filtered, and the filter cake was washed with ethyl acetate, the filtrate was washed with saline water and water, concentrated under reduced pressure, then recrystallized by ethyl acetate and n-hexane (2:1), to get 2.42 g of light yellow solid volasertib (I), with a yield of 78.3%.

Embodiment II

Under nitrogen atmosphere, 2-amino-7-ethyl-7,8-dihydro-5-methyl-8-isopropyl-(7R)-6(5H)-pteridinone (II) (1.17 g, 5 mmol), N-[trans-4-[4-(cyclopropylmethyl)-1-piperazinyl]cyclohexyl]-4-iodo-3-methoxybenzamide (III) (2.48 g, 5 mmol), cuprous iodide (142 mg, 0.75 mmol), 8-hydroxyisoquinoline (220 mg, 0.75 mmol), potassium carbonate (760 mg, 5.5 mmol) and 50 mL N,N-dimethylformamide were added to a three-necked bottle, heated to 100° C., stirred to dissolve, then added with ethylenediamine (45 mg, 0.75 mmol), continued to heat to 120° C., reacted for 8 hours, to complete the reaction detected by TLC. The resulting solution was cooled down to 50-60° C. and filtered, and the filter cake was washed with ethyl acetate, the filtrate was washed with saline water and water, concentrated under reduced pressure, then recrystallized by ethyl acetate and n-hexane (2:1), to get 2.64 g of off-white solid volasertib(I), with a yield of 85.4%.

Embodiment III 2-chloro-7-ethyl-7,8-dihydro-5-methyl-8-isopropyl-(7R)-6(5H) pteridinone (IV) (2.68 g, 10 mmol) and 25 mL of allylamine were added to a three-necked bottle, heated to reflux to react for 4 hours, to complete the reaction detected by TLC. The resulting solution was cooled down, added with 50 mL of pure water, and the mixture was extracted three times with methylene chloride. The organic phases were combined and dried over anhydrous sodium sulfate, and the solvent was recovered under reduced pressure. The resulting oily matter was 2-(N-allyl) amino-7-ethyl-7,8-dihydro-5-methyl-8-isopropyl-(7R)-6(5H) pteridinone (V), and dissolved in 50 mL of ethanol without treatment, and transferred to a dry three-necked reaction flask; under the nitrogen atmosphere, boron trifluoride etherate (0.9 g, 1 eq) and 5% palladium-carbon (0.3 g, 10% w/w) were added, heated to ethanol reflux for 9 hours, to complete the reaction detected by TLC. The solvent was recovered under reduced pressure, and the remnant was recrystallized by ethyl acetate, to get 2.25 g of light yellow solid 2-amino-7-ethyl-7,8-dihydro-5-methyl-8-isopropyl-(7R)-6(5H)-pteridinone (II), with a yield of 90.4%.

Embodiment IV 20 mL of tetrahydrofuran and trans-4-[4-(cyclopropylmethyl)-1-piperazinyl]cyclohexylamine trihydrochloride(VI) (3.47 g, 10 mmol) were added to a three-necked reaction flask, under ice-bath and stirring conditions, 20 mL of 3-methoxy-4-bromo-benzoyl chloride (VII) (2.72 g, 11 mmol) in tetrahydrofuran and 20 mL of diisopropylethylamine (6.45 g, 50 mmol) in tetrahydrofuran were added dropwise to react at room temperature for 5 hours, to complete the reaction detected by TLC. The solution was adjusted to pH 9-10 with 50% sodium hydroxide and extracted three times with methylene chloride. The organic phases were combined and washed once with saturated brine and water respectively, dried over anhydrous sodium sulfate and the solvent was recovered under reduced pressure. The remnant was recrystallized from isopropyl ether and dried in vacuo to get 3.88 g of off-white solid N-[trans-4-[4-(cyclopropylmethyl)-1-piperazinyl]cyclohexyl]-4-bromo-3-methoxybenzamide (III), with a yield of 86.4%.

Embodiment V 20 mL of tetrahydrofuran and trans-4-[4-(cyclopropylmethyl)-1-piperazinyl]cyclohexylamine trihydrochloride(VI) (3.47 g, 10 mmol) were added to a three-necked reaction flask, under ice-bath and stirring conditions, 20 mL of 3-methoxy-4-iodo-benzoyl chloride (VII) (2.72 g, 11 mmol) in tetrahydrofuran and 20 mL of diisopropylethylamine (6.45 g, 50 mmol) in tetrahydrofuran were added dropwise to react at room temperature for 5 hours, to complete the reaction detected by TLC. The solution was adjusted to pH 9-10 with 50% sodium hydroxide and extracted three times with methylene chloride. The organic phases were combined and washed with saturated brine and water once respectively, dried over anhydrous sodium sulfate and the solvent was recovered under reduced pressure. The remnant was recrystallized from methyl tert-butyl ether and dried in vacuo to get 4.08 g of off-white solid N-[trans-4-[4-(cyclopropylmethyl)-1-piperazinyl]cyclohexyl]-4-iodo-3-methoxybenzamide(III), with a yield of 82.1%.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

The invention claimed is:

1. A method for preparing volasertib comprising the step of reacting a compound of formula (II) with a compound of formula (III), wherein the structures of volasertib, formula (II) and formula (III) are shown as follows:

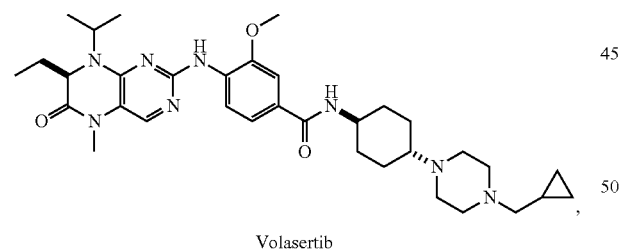

Volasertib

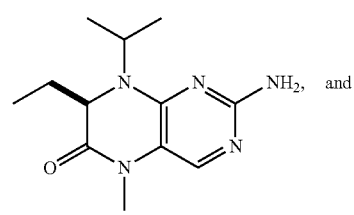

II and

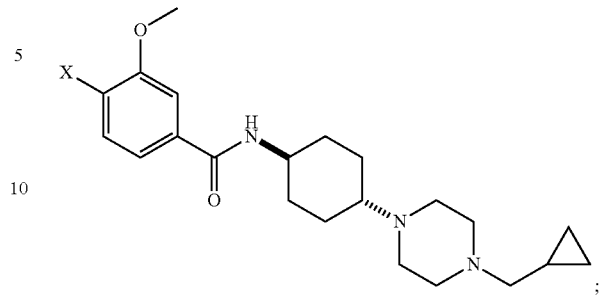

III wherein X is selected from the group consisting of fluorine, chlorine, bromine and iodine.

2. The method for preparing volasertib according to claim 1, wherein the preparation of the compound of formula (III) comprises the step of reacting trans-4-[4-(cyclopropylmethyl)-1-piperazinyl]cyclohexylamine trihydrochloride with 3-methoxy-4-halo-benzoyl chloride to get the compound of formula (III).

3. The method for preparing volasertib according to claim 1, wherein a halogen in the compound of formula (III) is fluorine, chlorine, bromine or iodine.

4. The method for preparing volasertib according to claim 1, wherein the step of reacting the compound of formula (II) with the compound of formula (III) is in the presence of a catalyst and optionally a cocatalyst; wherein the catalyst is cuprous iodide, zinc iodide, stannous chloride, palladium chloride, or silver iodide; and wherein the cocatalyst is 8-hydroxyquinoline, 2,6-dimethyl pyridine, 4-dimethylaminopyridine, N-methylmorpholine, N-ethylmorpholine, 1,5-diazabicyclo [4.3.0]-non-5-ene, 1,8-diazabicyclo [5.4.0]-undec-7-ene or 1,4-diazabicyclo [2.2.2] octane.

5. The method for preparing volasertib according to claim 1, wherein the step of reacting the compound of formula (II) with the compound of formula (III) is in the presence of a solvent and/or at a temperature; wherein the solvent is xylene, dioxane, dimethylsulfoxide, N,N-dimethylformamide or N,N-dimethylacetamide; and wherein the temperature is 100-160° C.

6. A compound of formula (II), wherein the structure of formula (II) is shown as follows:

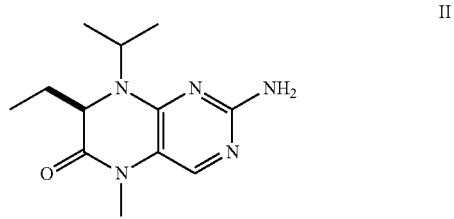

II

7. A method for preparing the compound according to claim 6, comprising the steps of subjecting 2-chloro-7-ethyl-7,8-dihydro-5-methyl-8-isopropyl-(7R)-6(5H)-pteridinone to an amination reaction to obtain 2-(N-allyl) amino-7-ethyl-7,8-dihydro-5-methyl-8-isopropyl-(7R)-6(5H)-pteridinone, and subjecting 2-(N-allyl) amino-7-ethyl-7,8-dihydro-5-methyl-8-isopropyl-(7R)-6(5H)-pteridinone to a reduction reaction to obtain the compound of formula (II).

8. A compound of formula (III), wherein the structure of formula (III) is shown as follows:

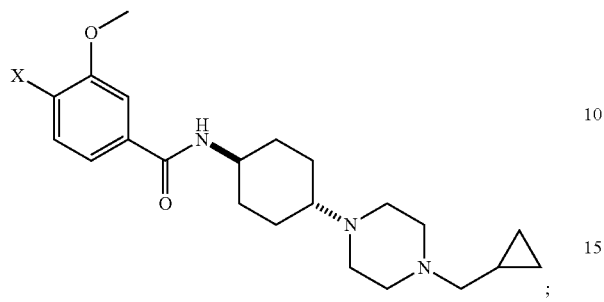

wherein X is selected from the group consisting of fluorine, chlorine, bromine and iodine.

9. A method for preparing the compound according to claim 8, comprising the step of reacting trans-4-[4-(cyclopropylmethyl)-1-piperazinyl]cyclohexylamine trihydrochloride with 3-methoxy-4-halo-benzoyl chloride to obtain the compound of formula (III).

* * * * *